US008256264B2

(12) United States Patent
Bosi et al.

(10) Patent No.: US 8,256,264 B2
(45) Date of Patent: Sep. 4, 2012

(54) METHOD AND DEVICE FOR DETECTING THE COMPOSITION OF GAS MIXTURES

(75) Inventors: Gildo Bosi, Imola (IT); Marco Remondini, Imola (IT); Ibanez Ricco', Imola (IT)

(73) Assignee: Sacmi Cooperativa Meccanici Imola Societa' Cooperativa, Imola (IT)

( * ) Notice: Subject to any disclaimer, the term of this patent is extended or adjusted under 35 U.S.C. 154(b) by 156 days.

(21) Appl. No.: 12/675,338

(22) PCT Filed: Nov. 26, 2008

(86) PCT No.: PCT/IB2008/003229
§ 371 (c)(1),
(2), (4) Date: Feb. 25, 2010

(87) PCT Pub. No.: WO2009/068965
PCT Pub. Date: Jun. 4, 2009

(65) Prior Publication Data
US 2010/0300180 A1    Dec. 2, 2010

(30) Foreign Application Priority Data
Nov. 29, 2007   (IT) .............................. BO2007A0788

(51) Int. Cl.
*G01N 21/00* (2006.01)

(52) U.S. Cl. ........................................... 73/1.06
(58) Field of Classification Search ...................... None
See application file for complete search history.

(56) References Cited

U.S. PATENT DOCUMENTS

| 4,269,057 A | 5/1981 | Ong et al. |
| 6,422,060 B1* | 7/2002 | Patashnick et al. .......... 73/28.01 |
| 7,096,715 B2* | 8/2006 | Kita et al. .................... 73/23.34 |
| 2005/0056079 A1 | 3/2005 | Nagy et al. |
| 2006/0042353 A1* | 3/2006 | Marquis et al. ................ 73/23.2 |
| 2009/0260423 A1* | 10/2009 | Munoz et al. ................ 73/61.71 |

FOREIGN PATENT DOCUMENTS
JP    410153562   *   6/1998
WO    0032091 A       6/2000

* cited by examiner

*Primary Examiner* — Robert R Raevis
(74) *Attorney, Agent, or Firm* — Pearne & Gordon LLP

(57) ABSTRACT

A method for detecting the composition of an unknown gas mixture ($M_{inc}$) through an electronic nose (2) equipped with a measuring chamber (3) that houses at least one sensor comprises the steps of: calibrating a sensor by feeding a known gas mixture ($M_n$) into the measuring chamber (3); feeding the unknown gas mixture ($M_{inc}$) into the chamber (3), while keeping the unknown gas mixture (Mine) in a predetermined desired state; and detecting the composition of the unknown gas mixture ($M_{inc}$) by means of the sensor.

25 Claims, 3 Drawing Sheets

METHOD AND DEVICE FOR DETECTING THE COMPOSITION OF GAS MIXTURES

TECHNICAL FIELD

This invention relates to a method and device for detecting the composition of an unknown gas mixture.

This invention relates in particular to a method and device for detecting the composition of an unknown gas mixture using an "electronic nose".

BACKGROUND ART

As is known, electronic noses are instruments which permit analysis, preferably continuous, of atmospheric air, and more in detail, make it possible to detect the components of a gas mixture, whether these components include odoriferous compounds or not, that is to say, whether these components can or cannot be detected by a human or animal olfactory system.

This specification refers to components with odoriferous compounds but without thereby limiting the scope of the invention.

Electronic noses can qualitatively classify the air analysed, assigning it to a specific olfative class, and olfactometrically quantify the air analysed by estimating its odour concentration.

An electronic nose mimics human olfaction and, generally speaking, its operation can be divided into the following stages:

detecting the gases using suitable sensors;
processing the signals from the sensors;
recognizing the odours.

The array of sensors is usually housed in a chamber made of a chemically inert material into which a reference gas (normally clean, i.e., odourless, air) is made to flow in order to create a reference measure for the subsequent processing of the sensor responses.

In use, the air to be analysed is delivered into the sensing chamber and produces a change in the chemical composition of the atmosphere and hence a different response from the sensors.

The measurement ends by injecting the reference gas into the sensing chamber again, cleaning the active material constituting the sensors so that the sensor response returns to the reference measurement.

In this specification, we refer to electronic noses equipped with metal oxide semiconductor (MOS) sensors but without thereby limiting the scope of the invention.

The principle on which these sensors are based is the variation in the electrical conductivity of the oxide in the presence of odoriferous substances compared to the value of this parameter under reference conditions.

During a generic measuring cycle, an electronic nose takes in the reference gas for a certain fraction of time and the air to be analysed for the remaining fraction.

Further, in prior art electronic noses, active carbons are used to clean the reference air and make it as odourless as possible.

However, electronic noses of this kind presents several disadvantages.

It is well known, for example, that the sensors they use are highly sensitive to changes in the temperature and humidity of the air to be analysed and of the reference air.

The dependence on environmental conditions makes reading of olfactive data difficult and definitely unreliable. Indeed, the temperature and humidity of the air can change considerably during the course of the day and from one season to another.

Moreover, the use of active carbons to clean the reference gas of possible contamination also tends to change the relative humidity of the gas itself.

For this reason, prior art electronic noses provide highly imprecise measurements and are unable to offer a high coefficient of repeatability.

DISCLOSURE OF THE INVENTION

This invention therefore has for an aim to overcome the above mentioned disadvantages by providing an odour detecting method and device that are both economical and reliable and that give precise measurements independently of the climatic conditions in which the measurements are taken.

The technical characteristics of the invention according to the aforementioned aim may be easily inferred from the contents of the appended claims, especially claim 1, and preferably any of the claims that depend, either directly or indirectly, on claim 1.

BRIEF DESCRIPTION OF THE DRAWINGS

Further, the advantages of the invention are apparent from the detailed description which follows, with reference to the accompanying drawings which illustrate preferred embodiments of the invention provided merely by way of example without restricting the scope of the inventive concept, and in which.

DETAILED DESCRIPTION OF THE PREFERRED EMBODIMENTS OF THE INVENTION

Figure 1:
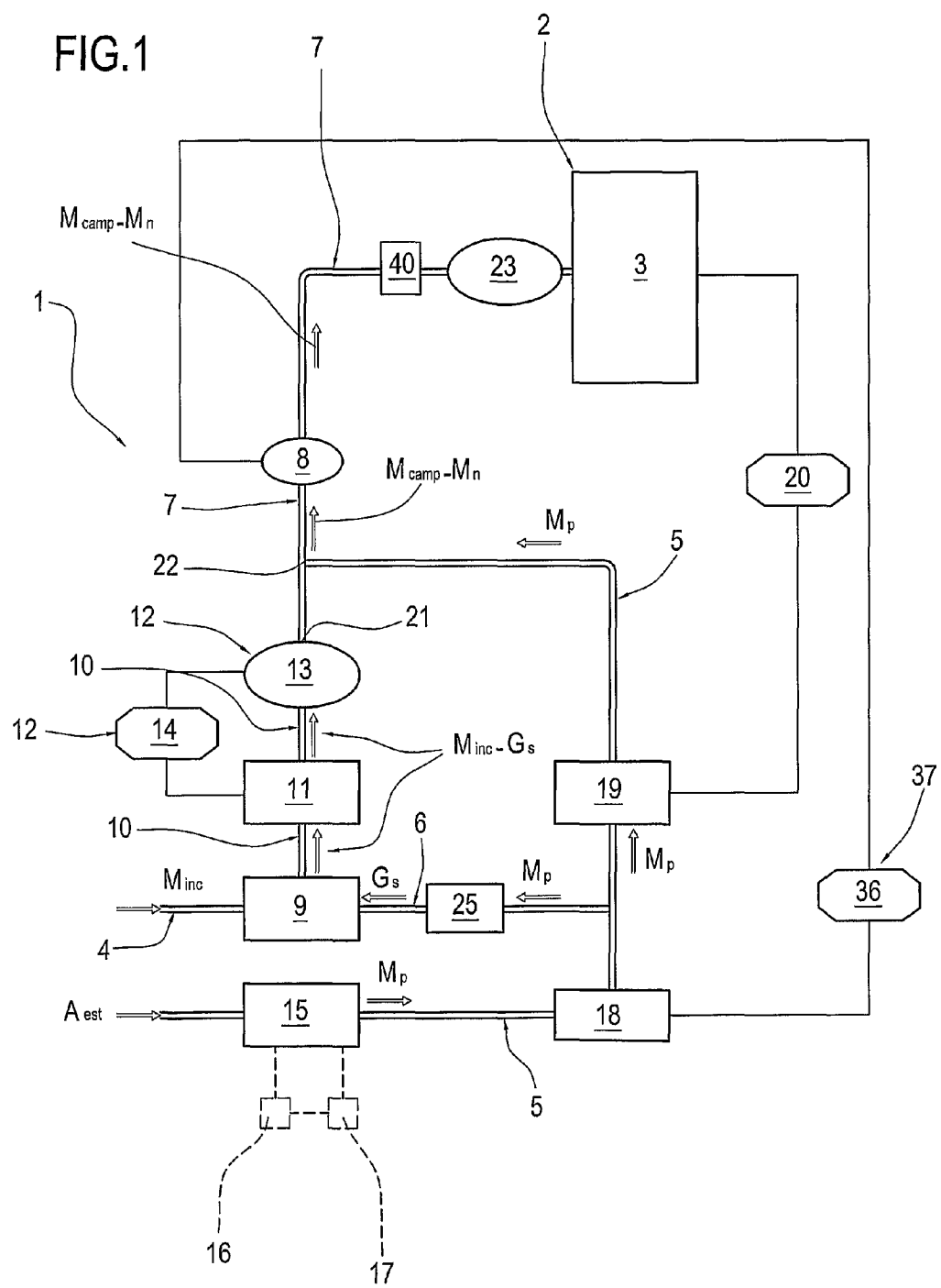
FIG. 1 illustrates an odour detection device made in accordance with this invention in a simplified block diagram to better understand the operation of the device.

With reference to FIG. 1, the numeral 1 denotes in its entirety an odour detection device schematically represented in blocks to better visualize the steps in the operation of the device 1 itself.

The device 1 comprises a prior art electronic nose schematically represented by the block 2 in FIG. 1.

The nose 2 comprises a measuring chamber 3 that houses a plurality of sensors of known type and therefore not illustrated.

The device 1 comprises a conduit 4 for feeding an unknown gas mixture ($M_{inc}$) including at least one compound to be detected by the electronic nose 2.

More in detail, the electronic nose 2 is designed to detect the composition of the unknown gas mixture $M_{inc}$ whether the olfative fingerprint of the compounds in the mixture $M_{inc}$ can be perceived by human or animal olfactory systems or whether the compounds in the mixture $M_{inc}$ cannot be perceived by human or animal olfactory systems.

The device 1 also comprises a conduit 5 for feeding a cleaning gas mixture $M_p$ and a conduit 6 for feeding a standard gas $G_s$.

The characteristics of each of these fluids are described in detail below.

The device 1 comprises a conduit 7 for feeding the above mentioned fluids into the measuring chamber 3.

On the fluid feed conduit 7 there is a temperature and humidity sensor 8 designed to measure the temperature and humidity of each of the fluids flowing in the conduit 7 towards the measuring chamber 3.

In addition, upstream of the measuring chamber 3, also on the conduit 7, there is a filter 40 delimited by an aluminium cover and connected to heating means, not illustrated, designed to heat the aluminium wall of the filter.

In the embodiment shown in FIG. 1, the unknown gas mixture $M_{inc}$ is sucked into the feed conduit 4 through customary suction means (not illustrated).

Also, in the embodiment shown in the accompanying drawings, the unknown gas mixture $M_{inc}$ consists of the air outside the device 1.

In other possible embodiments, not illustrated, the unknown gas mixture $M_{inc}$ might be fed to the conduit 4 from a sealed container containing a predetermined quantity of the unknown gas mixture $M_{inc}$ and may be any gas mixture whose composition is to be determined.

As shown in FIG. 1, at the outlet of the conduit 4 that feeds the unknown gas mixture $M_{inc}$ there is a switching solenoid valve 9.

The switching solenoid valve 9 is connected in mutually exclusive manner to the conduit 4 that feeds the unknown gas mixture $M_{inc}$ and to the conduit 6 that feeds the standard gas $G_s$.

The switching solenoid valve 9 is designed to selectively deliver the unknown gas mixture $M_{inc}$ or the standard gas $G_S$ to an intermediate conduit 10 connected to, and in fluid communication with, the conduit 7 that feeds the fluids to the measuring chamber 3.

On the intermediate conduit 10 there is a solenoid valve 11 for regulating the flow of the unknown gas mixture $M_{inc}$ and of the standard gas $G_s$.

The solenoid valve 11 is connected to means 12 for regulating the flow of the unknown gas mixture $M_{inc}$ and of the standard gas $G_s$.

The flow regulating means 12 comprise a flow meter 13 designed to measure the flow of the unknown gas mixture $M_{inc}$ or of the standard gas $G_s$ flowing through the intermediate conduit 10.

The means 12 also comprise a control device 14 for regulating the solenoid valve 11 in such a way that the unknown gas mixture $M_{inc}$ or the standard gas $G_s$ flows at a predetermined rate, defined below.

The conduit 5 that feeds the cleaning gas mixture $M_p$ comprises suction means (of known type and therefore not illustrated) for taking in the air $A_{est}$ from outside the device 1.

Downstream of the suction means, along the conduit 5, there is a unit 15 for cleaning and filtering the outside air $A_{est}$.

The unit 15 for cleaning and filtering the outside air $A_{est}$ comprises a catalyser 16 and an active carbon filter 17 (both drawn with dashed lines in FIG. 1).

In other possible embodiments, only the catalyser 16 or only the active carbon filter 17 is fitted.

The outside air $A_{est}$ flowing through the catalyser 16 and the active carbon filter 17 is cleaned of impurities and transformed into the cleaning gas mixture $M_p$.

The cleaning gas mixture $M_p$ thus consists of air from the outside environment with the impurities removed.

In other possible embodiments, the cleaning gas mixture $M_p$ might be any mixture that does not alter the response of the sensors or that alters it in a known and systematic manner so that the error due to the alteration can be compensated in the processing that follows the measurements performed by the sensors.

The device 1 also comprises a system 18 for conditioning the cleaning gas mixture $M_p$.

With reference to FIG. 1, downstream of the system 18 for conditioning the cleaning gas mixture $M_p$ there is a solenoid valve 19 for regulating the flow of the cleaning gas mixture $M_p$.

The solenoid valve 19 is connected to control means 20 for regulating the flow rate of the cleaning gas mixture $M_p$ in such a way a way as to keep the flow rate at a predetermined value.

The control means 20 operate in response to a flow meter 23 mounted on the conduit 7 upstream of the measuring chamber 3.

The conduit 5 for feeding the cleaning gas mixture $M_p$ is connected to, and in fluid communication with, the conduit 7 that feeds the fluids to the measuring chamber 3.

The fluid feed conduit 7 therefore has two inlets: a first inlet 21 located at the outlet of the intermediate conduit 10 and through which either the unknown gas mixture $M_{inc}$ or the standard gas $G_s$ is fed; and a second inlet 22, or junction 22, located at the outlet of the conduit 5 that feeds the cleaning gas mixture $M_p$.

In this way, as described in detail below, the feed conduit 7 selectively delivers to the measuring chamber 3 a known gas mixture $M_n$ composed of standard gas $G_S$ and cleaning gas mixture $M_p$, when the switching solenoid valve 9 opens the passage of the standard gas $G_s$, and a sample gas mixture $M_{camp}$, composed of unknown gas mixture $M_{inc}$ and cleaning gas mixture $M_p$, when the switching solenoid valve 9 opens the passage of the unknown gas mixture $M_{inc}$.

Thus, the sample gas mixture $M_{camp}$ is the result of mixing the unknown gas mixture $M_{inc}$ and the cleaning gas mixture $M_p$.

The standard gas $G_s$ is supplied from a source 25 of standard gas $G_S$. The standard gas $G_s$ is a gas having a known composition and is used to calibrate the electronic nose 2 before the measurements of the unknown gas mixture $M_{inc}$ are performed.

In the embodiment of FIG. 1, the source 25 of standard gas $G_s$ is a container containing a liquid having known composition and concentration.

The standard gas $G_s$ is formed by delivering into the container 25 a portion of the cleaning gas mixture $M_p$ fed by the conduit 5 and evaporating the liquid with the known composition (by heating it) in such a way that the flow of cleaning gas mixture $M_p$ inside the container absorbs a predetermined quantity of the standard evaporated liquid to form the standard gas $G_s$.

In other possible embodiments which are not illustrated, the standard gas $G_s$ is already in the gas state inside a container.

Figure 2:
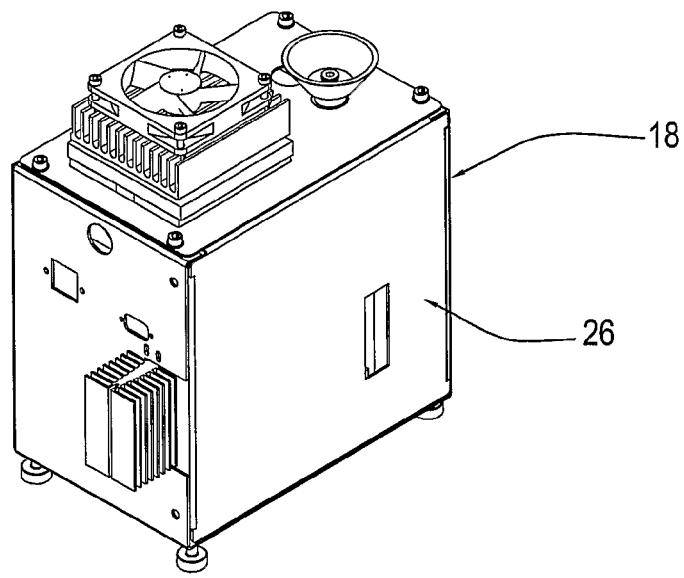
FIG. 2 is a schematic perspective view of a component of the device of FIG. 1.
Figure 3:
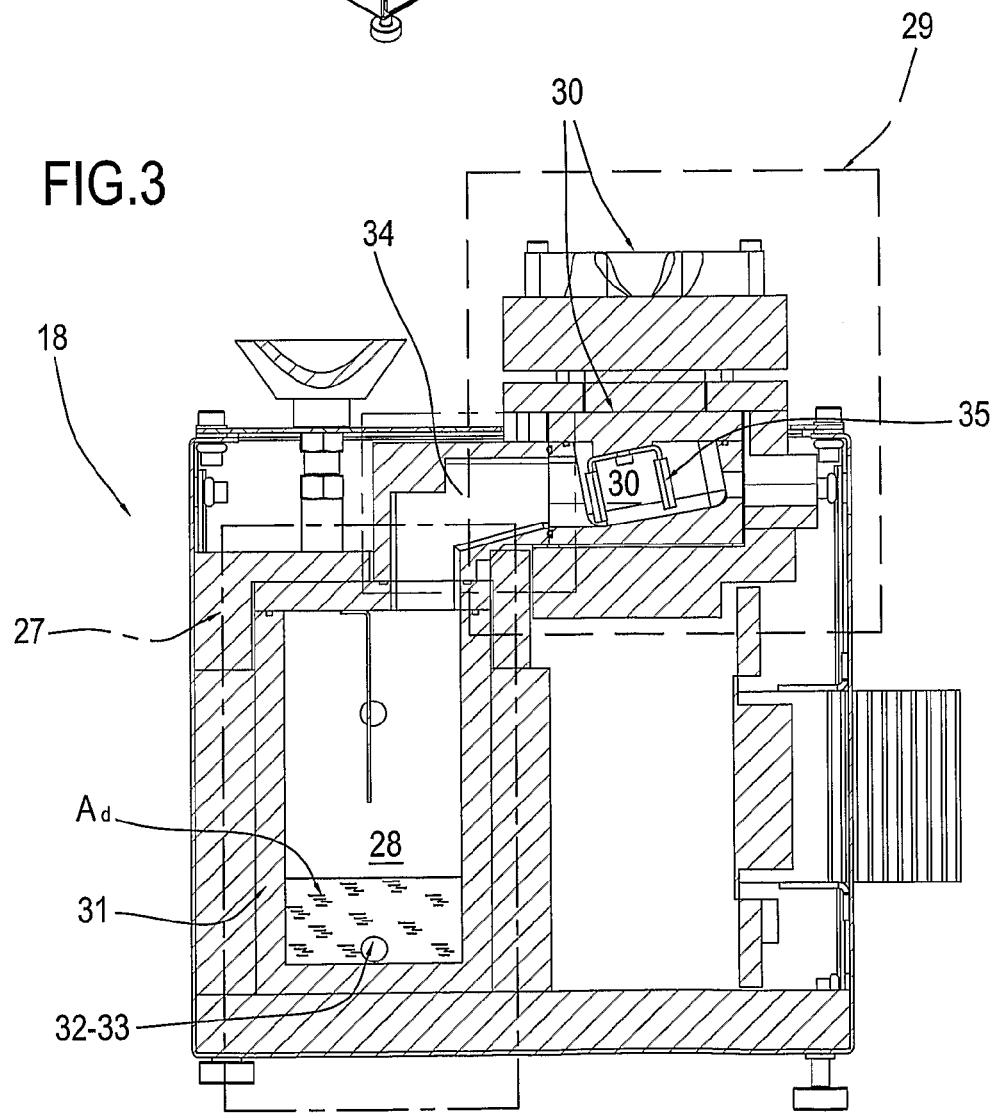
FIG. 3 is a schematic section view of the component of FIG. 2.

As shown in FIGS. 2 and 3, the conditioning system 18 is housed in a container 26 made of aluminium and insulated in such a way as to prevent heat loss to the outside environment, and is defined by a first module 27 comprising an evaporating chamber 28 and a second module 29 comprising a condenser 30.

The evaporating chamber 28 comprises a teflon-lined aluminium container 31 insulated so as not to transfer heat to the condenser 30.

The container 31 is heated by a heater 32 comprising heating elements 33.

The evaporating chamber 28 is partly filled with odourless distilled water $A_d$ and comprises a conduit 34 for discharging the cleaning gas mixture $M_p$, also made of teflon, and in fluid communication with the condenser 30.

The heating elements 33 heat the water $A_d$ on the bottom of the container 31 to a preset temperature so as to make a predetermined quantity of the water $A_d$ evaporate.

The condenser 30 comprises a heat exchanger 35 through which the cleaning gas mixture $M_p$ from the evaporating chamber 28 is condensed until the cleaning gas mixture $M_p$ reaches a predetermined humidity.

The system 18 also comprises means for collecting the condensed water in the condenser 30 and recycling it to the evaporating chamber 28.

In the embodiment illustrated in the accompanying drawings, the collecting means comprise the above mentioned conduit 34 which is shaped in such a way as to allow the condensed humidity to trickle down towards the evaporating chamber 28.

More in detail, the conduit 34 is inclined at an angle towards the evaporating chamber 28.

The gas mixture temperature and humidity sensor 8 is connected to a microprocessor-based control unit 36 (shown in FIG. 1) designed to regulate the temperature inside the condenser 30 and thus the degree of condensation of the cleaning gas mixture $M_p$ inside the condenser 30 itself, in such a way that the cleaning gas mixture reaches the required humidity, as described in detail below.

The control unit 36 constitutes means 37 which, in response to a signal from the sensor 8, regulate the degree of condensation of the cleaning gas mixture $M_p$ inside the condenser 30 by adjusting the temperature inside the condenser 30 itself.

The operation of the device 1 will now be described starting from a stand-by condition of the device 1 itself, where the sensors in the measuring chamber 3 are in a "response reset" state: this state is obtained by keeping the sensors in an atmosphere consisting of the cleaning gas mixture $M_p$.

The measuring cycle starts with the calibration of the sensors.

Sensor calibration is accomplished by feeding into the measuring chamber 3 the above mentioned known gas mixture $M_n$, composed of cleaning gas mixture $M_p$ and standard gas $G_s$.

The switching solenoid valve 9 is open to allow the standard gas $G_s$ to flow from the standard gas $G_s$ feed conduit 6 towards the intermediate conduit 10.

The standard gas $G_s$ flows along the intermediate conduit 10 and along the fluid feed conduit 7.

At the same time, a predetermined fraction of outside air $A_{est}$ is sucked into the conduit 5 that feeds the cleaning gas mixture $M_p$ and is made to pass through the cleaning and filtering unit 15.

The outside air $A_{est}$ is then transformed into cleaning gas mixture $M_p$ and is conditioned by the system 18, as described below.

The cleaning gas mixture $M_p$ is fed by the feed conduit 5 to the conduit 7.

At the inlet 22, the cleaning gas mixture $M_p$ and the standard gas $G_s$ are mixed to form the above mentioned known gas mixture $M_n$.

To keep the proportions of the known gas mixture $M_n$ constant, the flow of standard gas $G_s$ entering the conduit 7 is regulated by the regulating means 12 and the flow of cleaning gas mixture $M_p$ is regulated by the solenoid valve 19 controlled by the control means 20 associated with it and by the flow meter 23.

More in detail, the flow meter 23 detects the total flow of known gas mixture $M_n$ and, based on this value, regulates the flow of cleaning gas mixture $M_p$.

In the embodiment described in this specification, the known gas mixture $M_n$ is composed of 10% standard gas $G_s$ and 90% cleaning gas mixture $M_p$, but obviously, these values can be varied and are provided purely by way of non-limiting example of the device and method according to the invention.

Further, before entering the measuring chamber 3, the state of the known gas mixture $M_n$ is set and maintained at a predetermined, desired value.

More in detail, the term state of a mixture as used in this specification means the set of pressure, specific volume, temperature and humidity values of the gas mixtures used in the device.

This state is arbitrary and may be chosen and varied as required. The specific volume and pressure of the mixtures are regulated by means of known type and therefore not illustrated or described.

The temperature and humidity of the known gas mixture $M_n$ are regulated by the conditioning system 18.

In particular, the humidity and temperature sensor 8 measures the humidity and temperature of the known gas mixture $M_n$ and the conditioning system 18 varies the humidity of the cleaning gas mixture $M_p$ in such a way as to keep the humidity of the known gas mixture $M_n$ constant: if the humidity of the known gas mixture $M_n$ is less than the characteristic value of the desired state, then the humidity of the cleaning gas mixture $M_p$ is increased in order to increase the humidity of the known gas mixture $M_n$; on the other hand, if the humidity of the known gas mixture $M_n$ is greater than the characteristic value of the desired state, then the humidity of the cleaning gas mixture $M_p$ is decreased in order to decrease the humidity of the known gas mixture $M_n$ until the desired preset value is reached; in practice, regulating the humidity of the cleaning gas mixture $M_p$ compensates for the humidity of the known gas mixture $M_n$.

Feeding the known gas mixture $M_n$ into the measuring chamber 3 calibrates the sensors so they can measure the unknown gas mixture $M_{inc}$.

The filter 40 also regulates the temperature of the known gas mixture $M_n$ until the temperature of the known gas mixture $M_n$ corresponds to that of the required preset state.

Once the sensors have been calibrated, the unknown gas mixture $M_{inc}$ is fed into the measuring chamber 3.

More in detail, the unknown gas mixture $M_{inc}$, before entering the measuring chamber 3, is mixed with the cleaning gas mixture $M_p$ to form the above mentioned sample gas mixture $M_{camp}$.

The solenoid valve 9 is switched to shut off the passage of standard gas $G_s$ and to open the passage of unknown gas mixture $M_{inc}$ through the conduit 10.

The cleaning gas mixture $M_p$ continues to be fed by the conduit 5 as far as the inlet 22.

The sample mixture $M_{camp}$ composed of unknown gas mixture $M_{inc}$ and cleaning gas mixture $M_p$ is thus formed at the inlet 22.

The sample gas mixture $M_{camp}$ is composed of 50% unknown gas mixture $M_{inc}$ and 50% cleaning gas mixture $M_p$, but. obviously, these values can be varied and are provided purely by way of non-limiting example of the device and method according to the invention.

These proportions are maintained constant in the same way as the proportions of the known gas mixture $M_n$, described above and therefore not repeated.

The part of cleaning gas mixture $M_p$ present in the sample mixture $M_{camp}$ does not alter the response of the sensors for the purposes of the measurements to be performed on the unknown gas mixture $M_{inc}$.

In fact, the purpose of the cleaning gas mixture $M_p$ is to allow the state of the unknown gas mixture $M_{inc}$, to be controlled without altering the composition of the unknown gas mixture $M_{inc}$ itself.

In other words, the cleaning gas mixture $M_p$ is mixed with unknown gas mixture $M_{inc}$ to form the sample mixture $M_{camp}$, this sample mixture being simply the unknown gas mixture $M_{inc}$ diluted in known proportions without chemically altering the compounds to be measured.

The state of the sample mixture $M_{camp}$ (and, hence, also the state of the unknown gas mixture $M_{inc}$) is regulated and maintained constant at the predetermined desired state by regulating the state of the cleaning gas mixture $M_p$.

Once again, the filter 40 regulates the temperature of the sample gas mixture $M_{camp}$ until the temperature of the sample gas mixture $M_{camp}$ (and hence of the unknown gas mixture $M_{inc}$) corresponds to that of the required preset state.

The state of the cleaning gas mixture $M_p$ is regulated by the conditioning system 18.

More in detail, the humidity and temperature sensor 8 measures the humidity and temperature of the sample gas mixture $M_{camp}$ before the latter enters the measuring chamber 3 and the conditioning system 18 varies the humidity of the cleaning gas mixture $M_p$ in such a way as to keep the humidity of the sample gas mixture $M_{camp}$, (and hence of the unknown gas mixture $M_{inc}$) constant: if the humidity of the sample gas mixture $M_{camp}$ is less than the humidity value corresponding to that of the desired state, then the humidity of the cleaning gas mixture $M_p$ is increased in order to increase the humidity of the sample gas mixture $M_{camp}$; on the other hand, if the humidity of the sample gas mixture $M_{camp}$ is greater than the humidity value corresponding to that of the desired state, then the humidity of the cleaning gas mixture $M_p$ is decreased in order to decrease the humidity of the sample gas mixture $M_{camp}$ until the desired preset value is reached.

To vary the humidity of the cleaning gas mixture $M_p$, whether this is done to vary the humidity of the known gas mixture $M_n$ or the humidity of the sample mixture $M_{camp}$, the cleaning gas mixture $M_p$ is made to flow through the evaporating chamber 28, on the bottom of which there is odourless, distilled water $A_d$.

The water $A_d$, is heated by the heating elements 33, evaporates and is absorbed by the cleaning gas mixture $M_p$, raising the humidity of the latter to a value greater than the value the cleaning gas mixture $M_p$ must have when it leaves the condenser 30, calculated by the control unit 36.

The humidified cleaning gas mixture $M_p$ flows through the conduit 34 into the condenser 30 whose internal temperature is regulated by the control unit 36 based on feedback from the sensor 8 relating to the temperature and humidity of the known gas mixture $M_n$ or of the sample mixture $M_{camp}$ and processed by the control unit 36 itself.

The above mentioned desired state at which both the known gas mixture $M_n$ and the sample mixture $M_{camp}$ (and hence the unknown gas mixture $M_{inc}$) are regulated can be chosen arbitrarily.

In the embodiment described in this specification, this state coincides with the state of the unknown gas mixture $M_{inc}$, which is measured before the sensors are calibrated.

Alternatively, this state might coincide with the conditions of the atmospheric air outside the device 1 when the device 1 is used.

Figure 4:
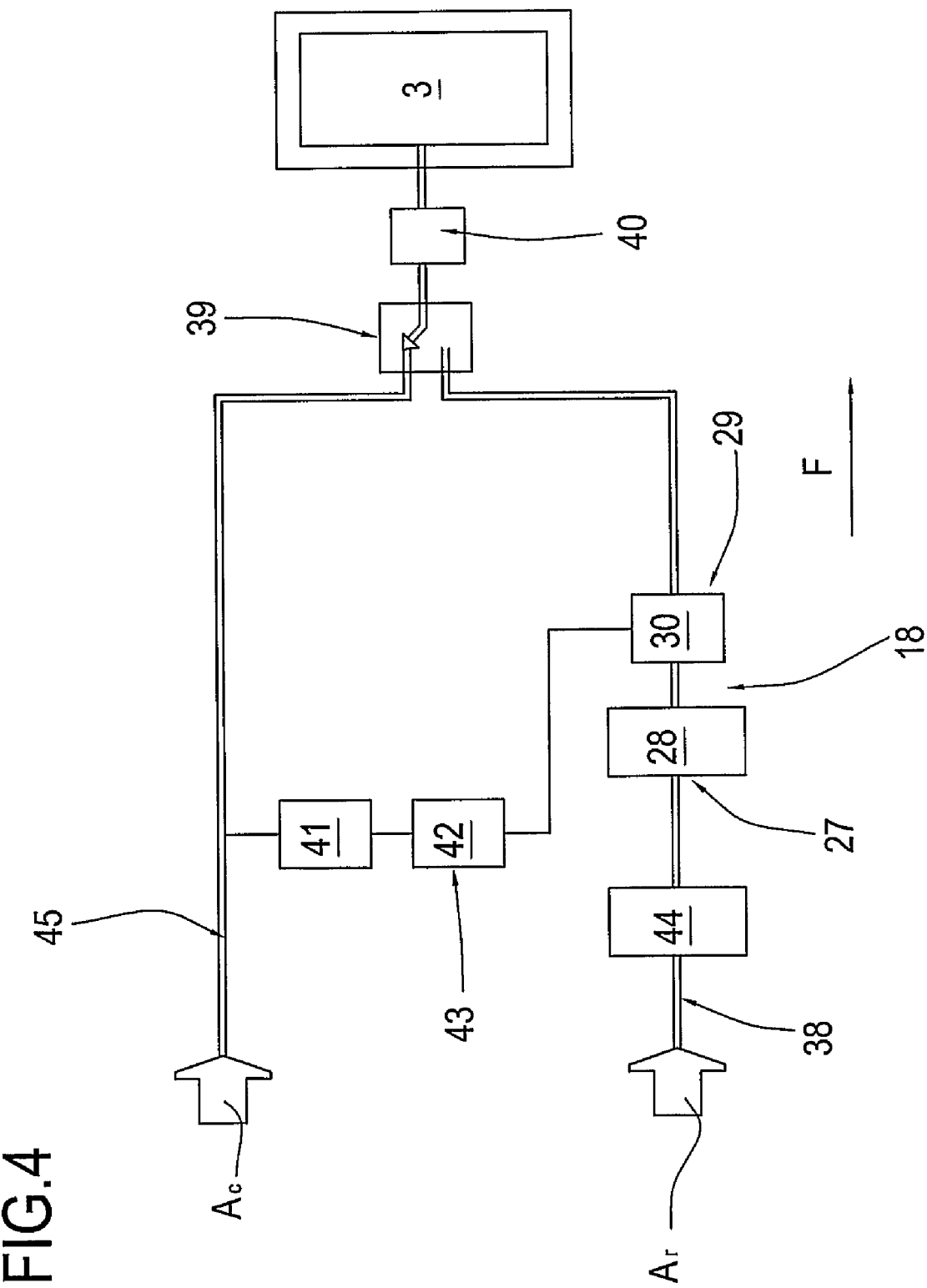
FIG. 4 illustrates an alternative embodiment of the odour detection device according to the invention in a simplified block diagram to better understand the operation of the device.

FIG. 4 shows a second embodiment of the device according to the invention.

In this embodiment, the unknown gas mixture consists of sample air $A_c$ and the known gas mixture consists of reference air $A_r$.

The measuring chamber 3 is connected to a conduit 45 for feeding the sample $A_c$ and to a conduit 38 for feeding the reference air $A_r$, with an interposed switching valve 39.

The switching valve 39, mounted upstream of the chamber 3 relative to the direction indicated by the arrow F in FIG. 4, selectively delivers the reference air $A_r$ and the sample air $A_c$ into the chamber 3.

The filter 40 is interposed between the switching valve 39 and the measuring chamber 3. The filter is delimited by an aluminium cover and is connected to heating means, not illustrated, designed to heat its aluminium wall.

The system 18 for conditioning the reference air $A_r$ is located upstream of the chamber 3, on the conduit 38 that feeds the reference air $A_r$.

The conduit 45 that feeds the sample air $A_c$ is associated with a sensor 41 for measuring the temperature and humidity of the sample air $A_c$.

The conditioning system 18 also comprises a microprocessor-based control unit 42, associated with the sensor 41 and designed to regulate the temperature inside the condenser 30 and, hence, the degree of condensation of the reference air $A_r$ inside the condenser 30 itself.

The control unit 42 constitutes means 43 for regulating the degree of condensation of the reference air $A_r$ inside the condenser 30 by adjusting the temperature inside the condenser 30 in response to a signal from the sensor 41.

In the embodiment illustrated in FIG. 4, the device 1 comprises an active carbon filter 44 located upstream of the conditioning system 18 relative to the direction of the arrow F in FIG. 4 and designed to clean the reference air $A_r$ flowing into the system 18 itself.

In an alternative embodiment that is not illustrated, instead of using as reference air $A_r$ the atmospheric air cleaned by the active carbon filter 44, the reference air $A_r$ might be supplied directly from a container of controlled, odourless air.

In use, a predetermined quantity of sample air $A_c$ is sucked into the feed conduit 45, where the sensor 41 measures the temperature and percentage of humidity of the sample $A_c$.

Based on these measurements, the control unit 42 determines the value, in degrees Celsius, of the dew point corresponding to the sample air $A_c$.

At the same time, a predetermined quantity of reference air $A_r$ is sucked into the conduit 38 that feeds the reference air $A_r$.

The air $A_r$ flows through the active carbon filters 44 which remove impurities from it.

After passing through the active carbon filters, the reference air $A_r$ flows into the conditioning system 18.

The reference air $A_r$ is made to flow through the evaporating chamber 28, on the bottom of which there is odourless, distilled water $A_d$.

The water $A_d$, is heated by the heating elements 33, evaporates and is absorbed by the reference air $A_r$, raising the humidity of the latter to a value greater than the value the reference air $A_r$ must have when it leaves the condenser 30, calculated by the control unit 42.

The humidified reference air $A_r$ flows through the conduit 34 into the condenser 30 whose internal temperature is regulated by the control unit 42 based on feedback from the sensor 41 relating to the temperature and humidity of the sample air $A_c$ and processed by the control unit 42 itself.

More in detail, the temperature inside the condenser 30 is equal to the dew point calculated for the sample air $A_c$: thus, the reference air $A_r$ leaving the condenser 30 is 100% water-saturated air at the temperature corresponding to the dew point of the sample air $A_c$ and hence the absolute humidity of the reference air $A_r$ is equal to the absolute humidity of the sample air $A_c$.

At this point, the switching valve 39 first of all allows the reference air $A_r$ to flow into the measuring chamber 3 where the sensors perform measurements on the air $A_r$.

Next, the switching valve 39 allows the sample air $A_c$ to flow into the measuring chamber 3, the sensors detect the characteristics of the air $A_c$ and the nose 2 detects odours by calculating the difference between the measurement performed on the reference air $A_r$ and the measurement performed on the sample air $A_c$.

The reference air $A_r$ and the sample air $A_c$ reach the same temperature as they flow through the heated aluminium filter 40 and into the measuring chamber 3 which is thermoregulated at a constant temperature; hence, inside the chamber 3, the sample air $A_c$ and the reference air $A_r$ have the same temperature and humidity (absolute and relative).

According to the embodiment described above, it is also possible to regulate the state of the sample air $A_c$ as a function of the temperature and humidity of the reference air $A_r$.

The invention has important advantages.

By regulating the state of the known gas mixture to calibrate the sensors and the state of the unknown gas mixture, using the conditioning system, it is possible to bring the two mixtures to, and maintain them at, a desired arbitrary state.

That means the composition of the unknown gas mixture can be measured extremely precisely and with a high degree of repeatability.

Furthermore, advantageously, the state of the known gas mixture is varied and brought to the desired state indirectly, that is to say, through a compensative variation of the state of the cleaning gas mixture.

Thus, the response of the sensors to the measurements which the sensors themselves are taking is not in any way altered and it is possible to obtain precise, repeatable results.

The invention claimed is:

1. A method for detecting the composition of an unknown gas mixture ($M_{inc}$) through an electronic nose (2) equipped with a measuring chamber (3) that houses at least one sensor, comprising the steps of:
   calibrating the at least one sensor by feeding a known gas mixture ($M_n$) into the measuring chamber (3);
   feeding the unknown gas mixture ($M_{inc}$) into the chamber (3), while keeping the unknown gas mixture ($M_{inc}$) in a predetermined desired state;
   detecting the composition of the unknown gas mixture ($M_{inc}$) by means of the at least one sensor,
wherein the method further comprises steps of
   mixing the unknown gas mixture ($M_{inc}$) with a cleaning gas mixture ($M_p$) to form a sample gas mixture ($M_{camp}$) and regulating the state of the cleaning gas mixture ($M_p$) in order to keep the sample gas mixture ($M_{camp}$) and hence the unknown gas mixture ($M_{inc}$) in the predetermined desired state, in such a way as to keep the humidity of the sample gas mixture $M_{camp}$, and hence of the unknown gas mixture $M_{inc}$ constant, and
   wherein the method further comprises a step of making the cleaning gas mixture ($M_p$) flow through a catalyser (16) before mixing the cleaning gas mixture ($M_p$) with the unknown gas mixture ($M_{inc}$).

2. The method according to claim 1, further comprising the steps of measuring the humidity and temperature of the sample gas mixture $M_{camp}$ via a humidity and temperature sensor (8) before the sample gas mixture $M_{camp}$ enters the measuring chamber (3) and varying the humidity of the cleaning gas mixture $M_p$ via a conditioning system (18) in such a way as to keep the humidity of the sample gas mixture $M_{camp}$ and hence of the unknown gas mixture $M_{inc}$ constant.

3. The method according to claim 1, wherein the step of calibrating the at least one sensor by feeding a known gas mixture ($M_n$) into the chamber (3) comprises the further step of keeping the known gas mixture ($M_n$) in the predetermined desired state.

4. The method according to claim 1, wherein the method further comprises the step of mixing a fraction of a standard gas ($G_s$) and a fraction of the cleaning gas mixture ($M_p$) to form the known gas mixture ($M_n$).

5. The method according to claim 4, wherein the step of calibrating the at least one sensor comprises a step of regulating the state of the cleaning gas mixture ($M_p$) in such a way as to keep the known gas mixture ($M_n$) in the desired state.

6. The method according to claim 1, wherein the state of the cleaning gas mixture ($M_p$) is regulated by a conditioning system (18).

7. The method according to claim 1, wherein the step of regulating the state of the cleaning gas mixture ($M_p$) comprises a step of delivering the cleaning gas mixture ($M_p$) into an evaporating chamber (28) on the bottom of which there is water heated by a heater (32, 33), the water evaporating and thus increasing the degree of humidity of the cleaning gas mixture ($M_p$).

8. The method according to claim 7, wherein the step of regulating the state of the cleaning gas mixture ($M_p$) comprises a step of delivering the cleaning gas mixture ($M_p$) leaving the evaporating chamber (28) into a condenser device (30) in such a way as to lower the degree of humidity of the cleaning gas mixture ($M_p$) to a preset value.

9. The method according to claim 1, wherein the method comprises a step of making the cleaning gas mixture ($M_p$) flow through a catalyser (16) before mixing the cleaning gas mixture ($M_p$) with a standard gas ($G_s$) to form the known gas mixture ($M_n$).

10. The method according to claim 1, wherein the method comprises a step of making the cleaning gas mixture ($M_p$) flow through an active carbon filter (17) before mixing the cleaning gas mixture ($M_p$) with the unknown gas mixture ($M_{inc}$) and with a standard gas ($G_s$).

11. The method according to claim 1, wherein the step of detecting the composition of the unknown gas mixture ($M_{inc}$) comprises a step of detecting an odoriferous compound in the unknown gas mixture ($M_{inc}$).

12. The method according to claim 1, where the unknown gas mixture ($M_{inc}$) is sample air ($A_c$) with unknown odour and the known gas mixture ($M_n$) is reference air ($A_r$), characterized in that the method comprises steps of:
   calibrating the sensor with the reference air ($A_r$);
   delivering a fraction of the sample air ($A_c$) into the chamber (3);
   detecting the unknown odour in the sample air ($A_c$);
   regulating the state of one of either the reference air ($A_r$) or the sample air ($A_c$) before both the sample air ($A_c$) and the reference air ($A_r$) flow into the chamber (3).

13. The method according to claim 12, wherein during the regulating step the state of the reference air ($A_r$) is regulated.

14. The method according to claim 13, wherein the step of regulating the state of the reference air ($A_r$) comprises a step of regulating the temperature and humidity of the reference air ($A_r$).

15. The method according to claim 13, wherein the step of regulating the state of the reference air ($A_r$) comprises a step of delivering the reference air ($A_r$) into an evaporating chamber (28) on the bottom of which there is water heated by a heater (32, 33), the water evaporating and thus increasing the degree of humidity of the reference air ($A_r$).

16. The method according to claim 15, wherein the step of regulating the reference air ($A_r$) comprises a step of delivering the reference air ($A_r$) leaving the evaporating chamber (28) into a condenser device (30) in such a way as to lower the degree of humidity of the reference air ($A_r$) to a preset value.

17. The method according to claim 16, wherein the method comprises a step of measuring the temperature and percentage of humidity of the sample air ($A_c$) before the sample air ($A_c$) flows into the measuring chamber (3).

18. The method according to claim 17, wherein the step of regulating the state of the reference air ($A_r$) is a function of the step of measuring the temperature and percentage of humidity of the sample air ($A_c$).

19. The method according to claim 17, comprising a step of regulating the degree of condensation of the reference air ($A_r$) inside the condenser device (30), wherein the step of regulating the degree of condensation of the reference air ($A_r$) inside the condenser device (30) is a function of the measured temperature and relative humidity of the sample air ($A_c$) so that the absolute humidity of the reference air ($A_r$) is substantially the same as the absolute humidity of the sample air ($A_c$).

20. The method according to claim 12, characterized in that the method comprises a step of making the temperature of the reference air ($A_r$) and that of the sample air ($A_c$) equal before the two types of air flow into the measuring chamber (3).

21. A method for detecting the composition of an unknown gas mixture ($M_{inc}$) through an electronic nose (2) equipped with a measuring chamber (3) that houses at least one sensor, comprising the steps of:
    calibrating the at least one sensor by feeding a known gas mixture ($M_n$) into the measuring chamber (3);
    feeding the unknown gas mixture ($M_{inc}$) into the chamber (3), while keeping the unknown gas mixture ($M_{inc}$) in a predetermined desired state;
    detecting the composition of the unknown gas mixture ($M_{inc}$) by means of the at least one sensor,
wherein the method further comprises steps of:
    mixing the unknown gas mixture ($M_{inc}$) with a cleaning gas mixture ($M_p$) to form a sample gas mixture ($M_{camp}$) and
    regulating the state of the cleaning gas mixture ($M_p$) in order to keep the sample gas mixture ($M_{camp}$) and hence the unknown gas mixture ($M_{inc}$) in the predetermined desired state, in such a way as to keep the humidity of the sample gas mixture $M_{camp}$, and hence of the unknown gas mixture $M_{inc}$, constant, and
wherein the unknown gas mixture ($M_{inc}$) is sample air ($A_c$) with unknown odour and the known gas mixture ($M_n$) is reference air ($A_r$), characterized in that the method comprises steps of:
    calibrating the sensor with the reference air ($A_r$);
    delivering a fraction of the sample air ($A_c$) into the chamber (3);
    detecting the unknown odour in the sample air ($A_c$);
    regulating the state of one of either the reference air ($A_r$) or the sample air ($A_c$) before both the sample air ($A_c$) and the reference air ($A_r$) flow into the chamber (3), and wherein during the regulating step the state of the reference air ($A_r$) is regulated, and wherein the step of regulating the state of the reference air ($A_r$) comprises a step of regulating the temperature and humidity of the reference air ($A_r$).

22. A method for detecting the composition of an unknown gas mixture ($M_{inc}$) through an electronic nose (2) equipped with a measuring chamber (3) that houses at least one sensor, comprising the steps of:
    calibrating the at least one sensor by feeding a known gas mixture ($M_n$) into the measuring chamber (3);
    feeding the unknown gas mixture ($M_{inc}$) into the chamber (3), while keeping the unknown gas mixture ($M_{inc}$) in a predetermined desired state;
    detecting the composition of the unknown gas mixture ($M_{inc}$) by means of the at least one sensor,
wherein the method further comprises steps of:
    mixing the unknown gas mixture ($M_{inc}$) with a cleaning gas mixture ($M_p$) to form a sample gas mixture ($M_{camp}$) and
    regulating the state of the cleaning gas mixture ($M_p$) in order to keep the sample gas mixture ($M_{camp}$) and hence the unknown gas mixture ($M_{inc}$) in the predetermined desired state, in such a way as to keep the humidity of the sample gas mixture $M_{camp}$, and hence of the unknown gas mixture $M_{inc}$ constant, and
wherein the unknown gas mixture ($M_{inc}$) is sample air ($A_c$) with unknown odour and the known gas mixture ($M_n$) is reference air ($A_r$), characterized in that the method comprises steps of:
    calibrating the sensor with the reference air ($A_r$);
    delivering a fraction of the sample air ($A_c$) into the chamber (3);
    detecting the unknown odour in the sample air ($A_c$);
    regulating the state of one of either the reference air ($A_r$) or the sample air ($A_c$) before both the sample air ($A_c$) and the reference air ($A_r$) flow into the chamber (3), and wherein during the regulating step the state of the reference air ($A_r$) is regulated, and
wherein the step of regulating the state of the reference air ($A_r$) comprises a step of delivering the reference air ($A_r$) into an evaporating chamber (28) on the bottom of which there is water heated by a heater (32, 33), the water evaporating and thus increasing the degree of humidity of the reference air ($A_r$), and wherein the step of regulating the reference air ($A_r$) comprises a step of delivering the reference air ($A_r$) leaving the evaporating chamber (28) into a condenser device (30) in such a way as to lower the degree of humidity of the reference air ($A_r$) to a preset value, and wherein the method comprises a step of measuring the temperature and percentage of humidity of the sample air ($A_c$) before the sample air ($A_c$) flows into the measuring chamber (3).

23. The method of claim 22, wherein the step of regulating the state of the reference air ($A_r$) is a function of the step of measuring the temperature and percentage of humidity of the sample air ($A_c$).

24. The method of claim 22, comprising a step of regulating the degree of condensation of the reference air ($A_r$) inside the condenser device (30), wherein the step of regulating the degree of condensation of the reference air ($A_r$) inside the condenser device (30) is a function of the measured temperature and relative humidity of the sample air ($A_c$) so that the absolute humidity of the reference air ($A_r$) is substantially the same as the absolute humidity of the sample air ($A_c$).

25. A method for detecting the composition of an unknown gas mixture ($M_{inc}$) through an electronic nose (2) equipped with a measuring chamber (3) that houses at least one sensor, comprising the steps of:
    calibrating the at least one sensor by feeding a known gas mixture ($M_n$) into the measuring chamber (3);
    feeding the unknown gas mixture ($M_{inc}$) into the chamber (3), while keeping the unknown gas mixture ($M_{inc}$) in a predetermined desired state;

detecting the composition of the unknown gas mixture ($M_{inc}$) by means of the at least one sensor, wherein the method further comprises steps of mixing the unknown gas mixture ($M_{inc}$) with a cleaning gas mixture ($M_p$) to form a sample gas mixture ($M_{camp}$) and regulating the state of the cleaning gas mixture ($M_p$) in order to keep the sample gas mixture ($M_{camp}$) and hence the unknown gas mixture ($M_{inc}$) in the predetermined desired state, in such a way as to keep the humidity of the sample gas mixture $M_{camp}$, and hence of the unknown gas mixture $M_{inc}$ constant; and wherein the unknown gas mixture ($M_{inc}$) is sample air ($A_c$) with unknown odour and the known gas mixture ($M_n$) is reference air ($A_r$), characterized in that the method comprises steps of:

calibrating the sensor with the reference air ($A_r$);

delivering a fraction of the sample air ($A_c$) into the chamber (3);

detecting the unknown odour in the sample air ($A_c$);

regulating the state of one of either the reference air ($A_r$) or the sample air ($A_c$) before both the sample air ($A_c$) and the reference air ($A_r$) flow into the chamber (3), and characterized in that the method comprises a step of making the temperature of the reference air ($A_r$) and that of the sample air ($A_c$) equal before the two types of air flow into the measuring chamber (3).

\* \* \* \* \*